United States Patent [19]

Benson

[11] Patent Number: 5,382,568
[45] Date of Patent: Jan. 17, 1995

[54] DECAPEPTIDE HAVING DOPAMINE STIMULATING ACTIVITY

[75] Inventor: Byrant Benson, Tucson, Ariz.

[73] Assignee: Arizona Board of Regents, Tucson, Ariz.

[21] Appl. No.: 125,503

[22] Filed: Sep. 22, 1993

Related U.S. Application Data

[63] Continuation of Ser. No. 747,782, Aug. 19, 1991, abandoned.

[51] Int. Cl.$^6$ ............ A61K 37/00; A61K 37/02; C07K 5/00; C07K 7/00
[52] U.S. Cl. .................................. 514/15; 530/378
[58] Field of Search ............ 514/15, 14; 530/327, 530/328

[56] References Cited

U.S. PATENT DOCUMENTS

| | | | |
|---|---|---|---|
| 3,933,782 | 1/1976 | Yardley | 530/328 |
| 3,941,763 | 3/1976 | Sarantakis | 530/313 |
| 4,253,997 | 3/1981 | Sarantakis | 530/313 |
| 4,307,083 | 12/1981 | Rivier et al. | 514/800 |
| 4,619,914 | 10/1986 | Vale, Jr. et al. | 530/313 |
| 4,667,017 | 5/1987 | Ishida | 530/402 |
| 4,800,191 | 1/1989 | Schally et al. | 530/313 |
| 4,801,577 | 1/1989 | Newton, Jr. et al. | 530/313 |

OTHER PUBLICATIONS

Atassi, M. Z. et al., *Proc. Natl. Acad. Sci.*, 86:6729-6733, Sep. 1989.
Kazim, L. et al., *Biochem J.*, 203; 201-208, 1982.
Kazim, L. et al., *Biochem. J., 191: 261-264, 1980.*
Beason, et al., *Advances in Pineal Research*, 4 (Eds. Reiter & Lukaszyk), pp. 99-111, 1990.
Benson, B., *Society for Neuroscience Abstracts*, 15:1277, 1989, from the 19th Ann. Mtg. of the Soc. for Neurasci, Oct. 29-Nov. 3, 1989.
Benson, B., et al., *Amer. Zool.*, 16:17-24, 1976.
Benson, B., et al., *Pineal Gland*, 2:165-187, 1981 (Ed Reiter).
Benson, B., et al., *Society for Neuoscience Abstracts*, 17:347, 1991, 21st Ann. Mt. of Soc. for Neursci; Nov. 10-15, 1991.
Benson, B. et al., *Int. J. Peptide Protein Res.*, 36: 109-121, 1990.
Remington's Pharmaceutical Sciences, (Ed. Gennaro et al.), pp. 1688-1691, 1990.

*Primary Examiner*—Robert J. Hill, Jr.
*Assistant Examiner*—Sheela J. Huff
*Attorney, Agent, or Firm*—Cahill, Sutton & Thomas

[57] ABSTRACT

The present invention discloses a novel, highly potent decapeptide of the formula:

$NH_2$-Ser-Phe-Pro-Thr-Thr-Lys-Thr-Tyr-Phe-Pro-COOH, or a synthetic analogue or pharmaceutically acceptable salt thereof, which compound inhibits the release of prolactin and luteinizing hormone by effecting increased turnover and release of the potent catecholamine and prolactin inhibiting factor dopamine, thereby regulating the release of gonadotropins and prolactin by the pituitary gland in mammals. The invention is also directed to various methods of use of the novel compound and to pharmaceutical compositions therefor.

10 Claims, 1 Drawing Sheet

SEQUENCE LISTING ( 1 ) GENERAL INFORMATION:

( i i i ) NUMBER OF SEQUENCES: 1

( 2 ) INFORMATION FOR SEQ ID NO: 1 :

( i ) SEQUENCE CHARACTERISTICS:
      ( A ) LENGTH: 10 amino acid residues.
      ( B ) TYPE: Amino acid
      ( C ) STRANDEDNESS: Unknown
      ( D ) TOPOLOGY: Unknown ( i i ) MOLECULE TYPE: Peptide ( i i i ) HYPOTHETICAL: No ( v ) FRAGMENT TYPE: N-terminal and internal fragments.

( v i ) ORIGINAL SOURCE:
      ( A ) ORGANISM: Bovine
      ( F ) TISSUE TYPE: Pineal gland ( x i ) SEQUENCE DESCRIPTION: SEQ ID NO: 1 :

Ser Phe Pro Thr Thr Lys Thr Tyr Phe Pro
      1               5                     10

DECAPEPTIDE HAVING DOPAMINE STIMULATING ACTIVITY

The present invention was made in the course of work conducted under Research Grant 5 R01 HD 19521, from the National Institute of Child Health and Human Development, Department of Health and Human Services, United States Public Health Service.

This application is a continuation of application Ser. No. 07/747,782 filed Aug. 19, 1991 now abandoned.

BACKGROUND OF THE INVENTION

The present invention relates to neurotropic peptides which effect increased turnover and release of the catecholamine dopamine, thereby regulating the release of gonadotropins and prolactin by the pituitary gland in mammals.

Peptides are compounds which contain two or more amino acids in which the carboxyl group of one acid is linked in peptide bond to the amino group of the other acid. Conventional representations of peptides are constructed such that the amino group appears to the left and the carboxyl group to the right; the position of the amino acid residues, usually identified by trivial names, are numbered from left to right as indicated in the example of a tripeptide below where R=the ionizing group of a specific amino acid

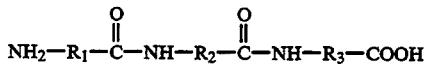

The pituitary gland is attached by a stalk to the region in the base of the brain known as the hypothalamus. The anterior portion of the pituitary secretes a number of protein hormones that travel through the bloodstream to reach other organs of internal secretion. In particular, the reproductive hormones follicle stimulating hormone (FSH) and luteinizing hormone (LH), collectively called gonadotropins, as well as prolactin (PRL), are released by the pituitary gland and stimulate the production of gametes and steroid hormones by the gonads.

Pituitary gonadotropins and prolactin are necessary for reproduction, and their secretion requires prior synthesis and release of hypothalamic factors such as gonadotropin hormone releasing hormone (GnRH) and catecholamines. The catecholamine norepinephrine (NE) stimulates GnRH release from the hypothalamus; in contrast, a second catecholamine dopamine (DA) generally inhibits GnRH release consequently reducing gonadotropin, prolactin and gonadal steroid secretion. In mammals, hypothalamic control of reproduction is modulated by yet another part of the brain, the epiphysis cerebri or pineal gland, which plays primarily an inhibitory or antigonadotropic role in several species.

Since the first reports of abnormal reproductive development in humans with pineal gland tumors (Huebner, O., Tsch. Med. Wschr. 24:214–222, 1898; Kitay, J. I. and M. D. Altschule, *The Pineal Gland,* Cambridge:Harvard Press, 1954), questions have been posed about the chemical nature of pineal hormones and particularly about the nature of the hormonal mediators of pineal antigonadotropic function. It is clear from modern investigations that the pineal gland regulates reproduction in most mammals through modulation of the hypothalamic-pituitary-gonadal axis in response to a number of environmental factors.

The pineal hormonal factors mediating this function vary among species. For example, in the hamster and sheep, indolic compounds derived from serotonin may convey the pineal's hormonal message to the hypothalamus, whereas this is not the case in the more commonly employed laboratory rat. Early work in this area suggested that in the human, rat and mouse the pineal antigonadotropic factor is proteinaceous in character (for review see: Benson, B. and I. Ebels, In: *The Pineal Gland,* Ed. by R. J. Reiter, CRC Press, Boca Raton, pp.165–187, 1981); more recent investigations suggest that this antigonadotropin acts by stimulation of hypothalamic dopamine synthesis (Benson, B. et al., in: *Role of Peptides and Proteins in Control of Reproduction,* Ed. by S. M. McCann and D. S. Dhindsa, Elsevier Sci. Pub. Co., N. Holland, pp. 111–130, 1933; Benson, B. et al., in: *Advances In Pineal Research,* Vol. 4, Ed. by R. J. Reiter and A. Lukaszyk, Libbey & Co., Ltd., pp. 99–111, 1990).

For many years investigators have searched for potent antagonists of GnRH, the hypothalamic decapeptide that regulates pituitary secretion of gonadotropins (M. Karten and Je. E. Rivier, Endocrine Reviews 7:44–66, 1986). The high degree of interest in such antagonists is due to their usefulness in the fields of reproductive endocrinology, gynecology, contraception and oncology. In general most prior art GnRH antagonists are GnRH analogs in which the GnRH amino acid sequence has been modified by the deletion and/or replacement of key amino acids, particularly those at positions 2 or 6. See, for example, the United States patents listed below.

| U.S. PAT. NO. | INVENTOR | ISSUE DATE |
|---|---|---|
| 3,933,782 | Yardley | 01/20/76 |
| 3,941,763 | Sarantakis | 03/02/76 |
| 4,253,997 | Sarantakis | 03/03/81 |
| 4,307,083 | Rivier et al. | 12/22/81 |
| 4,619,914 | Vale et al. | 10/28/86 |
| 4,800,191 | Schally et al. | 01/24/89 |
| 4,801,577 | Nestor et al. | 01/31/89 |
| 4,866,160 | Coy et al. | 09/12/89 |

The desired GnRH analogs are those that bind to the GnRH receptor and block endogenous GnRH access to the receptor, thus rendering endogenous GnRH ineffective.

In contrast to the prior art GnRH antogonists, the pineal antigonadotropin of the present invention effects GnRH antagonism via a different mechanism, viz. by inhibition the release of GnRH from the hypothalamus. The distinction between the prior art and the present invention is illustrated in FIG. 1, which is a diagram of the hormonal control of reproduction. Because the inhibition is accomplished by increased turnover and release of catecholamines including the potent prolactin inhibiting factor dopamine, pituitary prolactin secretion is concomitantly reduced by the pineal antigonadotropin. The potential utility of the pineal antigonadotropic peptide of the present invention extends therefore beyond the uses in reproductive endocrinology mentioned above to other areas of neuroscience, including neuropathological states such as Parkinson's and Alzheimer' disease which may be caused by deficits in catecholaminergic neurotransmitters.

SUMMARY OF THE INVENTION

The present invention relates in one embodiment to a novel and highly potent decapeptide which inhibits the release of prolactin and luteinizing hormone by effecting increased turnover and release of the potent catecholamine and prolactin inhibiting factor dopamine. The invention is also directed to various methods of use of the novel compound and to pharmaceutical compositions and methods of use therefor.

More specifically, the present invention relates to compounds of the formula:

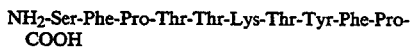

NH₂-Ser-Phe-Pro-Thr-Thr-Lys-Thr-Tyr-Phe-Pro-COOH or a synthetic analogue or pharmaceutically acceptable salt thereof.

It is an object of the present invention to provide compounds which effect increased turnover and release of dopamine.

It is an object of the present invention to provide a peptide which inhibits the release of prolactin & luteinizing hormone.

It is another object of the present invention to provide a method of inhibiting the release of hormones necessary to the reproductive cycle, substantially free of the deleterious side effects commonly associated with steroid-based methods of reproductive inhibition.

It is another object of the present invention to provide a method of treating neuropathogical states caused by deficiencies in catecholaminergic neurotransmitters.

These and other objects of the present invention will become more apparent from the following detailed description.

ABBREVIATIONS AND DEFINITIONS

Figure 1:
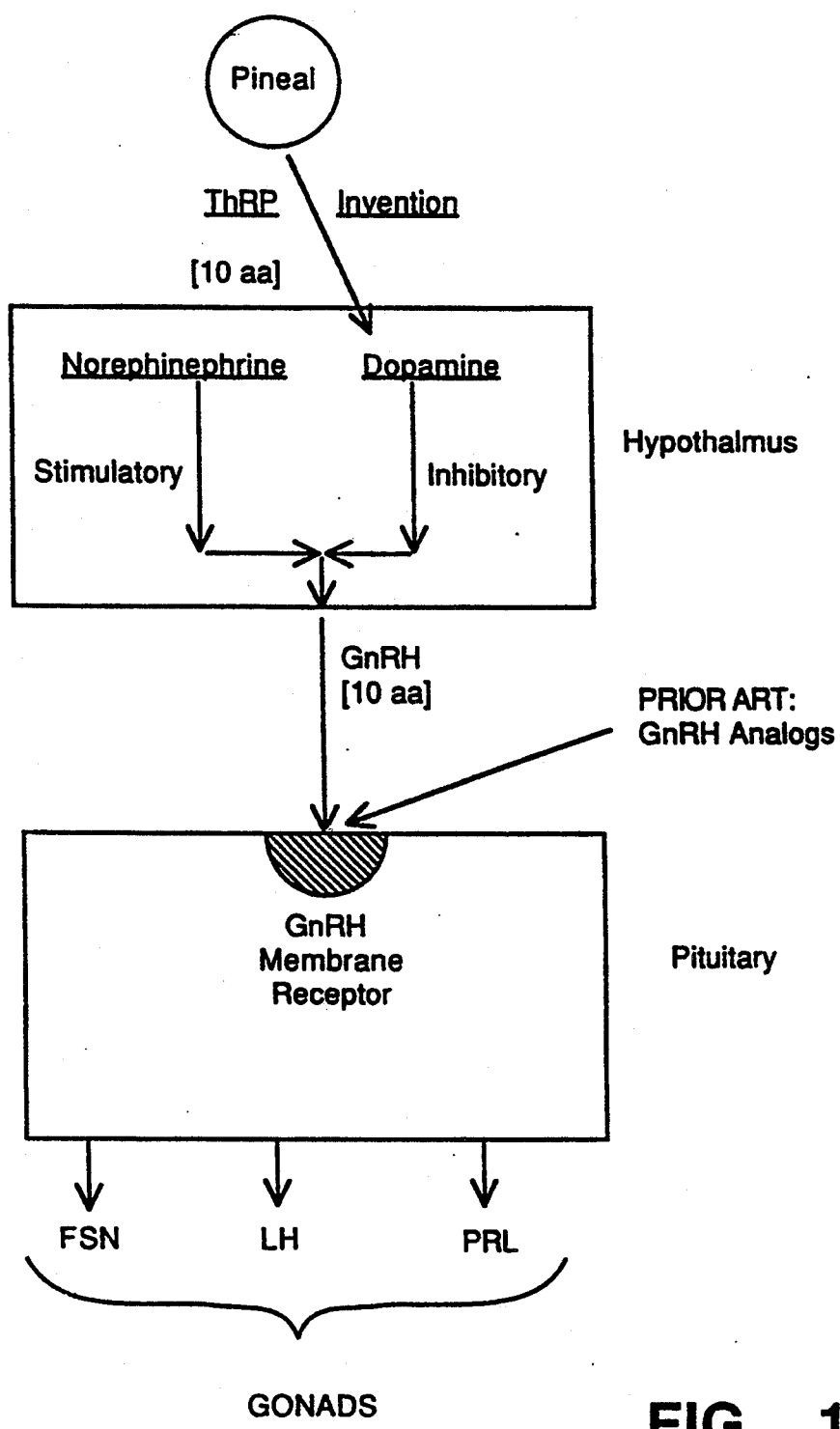
FIG. 1 is a simplified diagram of the hormonal control of reproduction.

For convenience in describing the present invention, the conventional abbreviations for the nomenclature used to define peptides as specified by the IUPAC-IUB Commission on Biochemical Nomenclature (European J. Biochem. 138:9–37, 1984) will be used. In accordance with conventional representation, the amino groups at the N-terminus appears to the left and the carboxyl group at the C-terminus to the right. The abbreviations for the amino acid residues found in the pineal antigonadotropin are based on the trivial names of the amino acids and are: Lys, lysine; Phe, phenylalanine; Pro, proline; Ser, serine; Thr, threonine; and Tyr, tyrosine. The systemic names are given below. All amino acids discussed are of the L-series unless stated otherwise.

Other abbreviations used are:
ACN=acetonitrile; a common solvent in peptide HPLC
C=carbon atom
$CO_2$=carbon dioxide
COOH=a monovalent radicle called a carboxyl group
Cys=cysteic acid
FSH=follicle stimulating hormone; a glycoprotein hormone secreted by the pituitary which stimulates follicle and ovum development, estrogen production in females and spermatogenesis in males.
GnRH=a gonadotropin releasing decapeptide produced in the hypothalamus which stimulates pituitary release of LH and FSH; synonyms used are LHRH, LRF and LRH
HPLC=high performance liquid chromatography
LH=luteinizing hormone; a pituitary glycoprotein which stimulates ovulation, ovarian luteinization and progesterone production in females, and testosterone production and spermatogenesis in males.
Lys=lysine; 2-6-diaminohexanoic acid
M=mole or molar
min=minute or minutes
mL=milliliter
$M_r$=molecular weight
N=nitrogen
$NH_2$=monovalent amino group
$NH_2C_2H_3O_2$=ammonium acetate, used for ion pairing in HPLC
nm=nanometers
PAG=pineal antigonadotropin or antigonadtropic decapeptide isolated from pineal glands
Phe=phenylalanine; 2-amino-3-phenylpropanoic acid
Pro=proline; pyrrolidine-2-carboxylic acid
PRL=prolactin; a glycoprotein produced by the pituitary gland that stimulates breast development and lactation, and augments gonadal steroid secretion.
Ser=serine; 2-amino-3-hydroxypropanoic acid
TFA=trifluoroacetic acid; a common HPLC solvent
Thr=threonine; 2-amino-3-hydroxybutanoic acid
Tyr=tyrosine; 2-amino-3-(4-hydroxyphenyl)propanoic acid
UV=ultraviolet
v/v=volume per volume As used herein, the term "pharmaceutically acceptable salts" refers to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like: and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) base addition salts formed with polyvalent metals cations such as zinc, calcium, bismuth, barium magnesium, aluminum, copper, cobalt, nickel, cadmium, and the like; or with an organic cation formed from N,N' -dibenzylethylene-diamine or ethylenediamine; or (c) combinations, of (a) and (b), e.g., a zinc tannate salt and the like.

DETAILED DESCRIPTION OF THE INVENTION

In one embodiment, the present invention is a substantially pure decapeptide having the following amino acid sequence: NH₂-Ser-Phe-Pro-Thr-Thr-Lys-Thr-Tyr-Phe-Pro-COOH, and synthetic analogues and nontoxic salts thereof.

PREPARATION OF PINEAL ANTIGONADOTROPIC PEPTIDE

The non-indolic antigonadotropic peptide of the present invention was found in human, bovine, ovine and rat pineal glands. For partial purification of the antigonadotropin on a large scale, fresh bovine or ovine pineal glands were collected fresh at the abattoir, frozen on solid $CO_2$ and maintained between $-60°$ and $-80°$ C. before extraction. The extraction and partial purification of the pineal antigonaodtropin followed standard methods for peptide isolation: Benson, et al., Int. J. Peptide Protein Res. 36:109-121,1990. Purification and structure elucidation steps follow:

Extraction 1. 150 g batches of frozen glands were freeze-dried and the lyophilizate pulverized and ground to a fine powder in a mechanical blender. The powdered glands were defatted by stirring in 500 mL of acetone at room temperature for 30 min. The acetone was removed by vacuum filtration through Whatman #1 paper with recovery of the residue. This procedure was repeated twice with acetone and twice again with methylene chloride. The defatted residue was thoroughly desiccated in vacuo.

2. The dried, defatted residue was homogenized with a Tekmar Tissumizer at 1.0° C. in 250 mL of 0.2N acetic acid containing $10^{-6}M$ Pepstatin A. Homogenates were centrifuged at $10,000 \times G$ at 4° C. for 20 min and the pellets rehomogenized three additional times with the same quantities of 0.2N acetic acid/Pepstatin A and centrifuged as before. The supernatant fractions were combined, stirred overnight at 4° C. and centrifuged at $10,000 \times G$ for 20 min. After vacuum filtration through Whatman #41 paper fitted in a Buchner Flask, the supernatant fractions served as starting material for subsequent ultrafiltration.

Ultrafiltrations I & II

The filtered extracts were serially ultrafiltered in 0.2N acetic acid through Amicon membranes XM300 and YM30 ($M_r$ cutoffs at 300,000 and 30,000, respectively) at 4° C. under low $N_2$ pressure (<20 psi). YM30 filtrates containing the peptides of interest ($M_r < 30,000$) were divided into two portions, concentrated by lyophilization and stored at $-80°$ C. before further fractionation by gel filtration chromatography on Sephadex G-25.

Sephadex chromatography

1. Concentrated ultrafiltration YM30 filtrates, representing the residues from 75 g wet weight equivalents of pineal glands, were chromatographed at 4° on $5 \times 95$ cm Sephadex G-25 (fine) columns equilibrated and eluted with 0.2N acetic acid.

2. Fractions were collected over a ten min period per tube at a flow rate of 20 drops/min. Column eluents were monitored at 280 nm, and fractions pooled according to observed peaks. Molecular size markers included Dextran Blue ($M_r$ $2 \times 10^3$), ribonuclease ($M_r$ $14 \times 10^3$) and Bacitracin ($M_2$ $1.4 \times 10^3$).

3. Under the conditions described above the pineal antigonadotropic peptide was located by association with two peaks of 280 nm absorbance: one with a retention time between 1.6 and $1.8 \times 10^3$ min (in association with proteins of approximate 10,000-15,000 $M_r$) and a second peak that had a retention time between 2.6 and $2.8 \times 10^2$ min (in mixture with other compounds of $M_r$ between 500 and 1500). The individual fractions collected in association with these two absorbance peaks were pooled and concentrated by lyophilization.

Ultrafiltrations III, IV and V

The lyophilized, pooled fractions from Sephadex chromatography containing the antigonadotropic peptide were taken up in 5% formic acid and further fractionated by serial ultrafiltration at 4° through Amicon membranes YM10, YM2 and UM05. In this manner peptides bound to larger proteins were dissociated, passed through the YM10 and YM2 membranes and localized to the UM05 retentate in mixture with compounds of $M_r > 500$. In addition to further purification, this step effectively removed salts and other low $M_r$ materials. The UM05 residue containing the antigonadotropin was lyophilized and stored at $-80°$ C.

Purification by High Performance Liquid Chromatography (HPLC)

A chromatographic system consisting of a Spectra-Physics model SP8800-010 ternary gradient pump with semipreparative heads, a Rheodyn model 7125, 1.0 mL volume loop injector and a model SP4290-010 computing integrator was used with a Waters model 450 variable wavelength UV detector. Peptides in column eluents were detected at 210 nm; fractions were collected with a Buchler Fractomette model 400 fraction collector.

Lyophilized UM05 retentates from Sephadex G-15 fractions containing the antigonadotropin were further fractionated by sequential semipreparative HPLC. Several chromatographic procedures utilized ternary gradients with the aqueous buffer coded "A", the organic solvent coded "B" and a mixture of each as mobile phase "C". Each mobile phase was degassed in vacuo while stirred for ten minutes and sparged with helium gas.

HPLC 1

Initial HPLC of quantities of UM05 retentates representing the purified residue from 65 g wet weight of starting pineal glands was performed on a $1.0 \times 25.0$ cm, 300 Angstrom semipreparative C-8 column (Rainin Dynamax) at flow rates of 8.0 ml/min. Residues were dissolved in mobile phase, filtered through a 0.45 micron filter and serially injected in volumes of 0.5-0.8 ml. Column eluates were routinely monitored at 210 nm and fractions were collected. Solvent A: 0.01M trifluoroacetic acid (TFA); solvent B: 0.01M TFA in acetonitrile (ACN):$H_2$ (50:50, v/v). Binary gradients were employed in the following configuration:

| Time (min): | 0 | 20 | 40 | 45 | 46 | 50 |
|---|---|---|---|---|---|---|
| % Sol. A: | 88 | 75 | 50 | 0 | 0 | 88 |
| % Sol. B: | 12 | 25 | 50 | 100 | 100 | 12 |

Under these conditions significant amounts of the antigonadotropin of interest were eluted with a retention between 25 and 35 min. A synthetic oxytocin standard may be applied to the column as a marker because it should also be eluted within this same retention time. The fractions collected between 25 and 35 min were pooled from separate chromatographic runs, concentrated by rotary evaporation, lyophilized and stored at $-80°$ C. until further purification.

HPLC 2

Secondary HPLC of the residue containing the antigonadotropin from the first HPLC described above was carried out on a 60 Angstrom, semipreparative C-8 column (Rainin Dynamax). Amounts representing 425 g wet weight starting pineal gland equivalents were injected in 0.9 ml volumes. Solvent A: 0.01 TFA in ACN; solvent B: 0.01M TFA: solvent C: 0.01M TFA in H₂O:ACN (1:1, v/v). HPLC was performed with these ternary gradients at a flow rate of 2.5 ml/min and mobile phase components changing as indicated:

| Time (min): | 0 | 33 | 38 | 40 | 45 | 50 | 55 | 58 |
|---|---|---|---|---|---|---|---|---|
| % Sol. A: | 0 | 0 | 0 | 0 | 0 | 0 | 15 | 40 |
| % Sol. B: | 80 | 45 | 45 | 43 | 30 | 10 | 0 | 0 |
| % Sol. C: | 20 | 55 | 55 | 57 | 70 | 90 | 85 | 60 |

Under these conditions the antigonadotropin was eluted with a retention time between 32 and 35 minutes, again in the volume containing an oxytocin standard. The fractions collected within this retention time were pooled, lyophilized and saved for further purification by HPLC.

HPLC 3

Antigonadotropic peptides in the lyophilized residues from the secondary HPLC were further separated on the 60 Angstrom C-8 column by ternary gradient HPLC with mobile phases which included methanol and ammonium acetate as ion-pairing reagent. Solvent A: ACN:methanol, 2:1 (v/v) in 0.01M TFA; solvent B: 15% solvent A and 85% 30 mM NH₄C₂H₃O₂ in 0.01M TFA; solvent C: 50 solvent A and 50% 30 mM NH₄C₂H₃O₂ in 0.01M TFA. This chromatography was performed at a flow rate of 2.3 ml/min with mobile phase composition programmed to change as follows:

| Time (min): | 0 | 30 | 40 | 45 | 50 | 53 | 60 |
|---|---|---|---|---|---|---|---|
| % Sol. A: | 0 | 0 | 0 | 0 | 30 | 30 | 0 |
| % Sol. B: | 88 | 70 | 50 | 40 | 0 | 0 | 88 |
| % Sol. C: | 12 | 30 | 50 | 60 | 70 | 70 | 12 |

Under these conditions the antigonadotropin was eluted between 42 and 52 min; the fractions collected within this range of retention times were pooled, lyophilized and subjected to additional chromatography.

HPLC 4

The lyophilized residue from the tertiary chromatography described above were re-chromatographed on the 60 Angstrom C-8 semipreparative column with the same solvents as described for HPLC 3. Ternary gradient mobile composition was programmed to change as follows:

| Time (min): | 0 | 10 | 25 | 28 | 40 | 45 |
|---|---|---|---|---|---|---|
| % Sol. A: | 0 | 0 | 10 | 30 | 30 | 0 |
| % Sol. B: | 50 | 50 | 20 | 0 | 0 | 50 |
| % Sol. C: | 50 | 50 | 70 | 70 | 70 | 50 |

Under these conditions the pineal antigonadotropic peptide was eluted in a large 210 nm absorbance peak with a retention time of 32.29 min. The fractions in the range of this retention time (between 28 and 34 min) were pooled, lyophilized and stored at −80° C. until final chromatography.

HPLC 5

Final isolation of the antigonadotropin was accomplished by HPLC on the 60 Angstrom C-8 column with changes in the composition of the mobile phase. Solvent A: 0.04M TFA in methanol; solvent B: 15% 0.04M TFA and 85% 0.04M TFA in methanol/ACN (4:1, v/v); solvent C: 50% 0.04M TFA and 50% 0.04M TFA in methanol/ACN (4:1, v/v). The column was eluted at a flow rate of 2.0 ml/min with the ternary gradient mobile phase changed as follows:

| Time (min): | 0 | 35 | 40 | 45 |
|---|---|---|---|---|
| % Sol. A: | 0 | 20 | 20 | 0 |
| % Sol. B: | 50 | 0 | 0 | 50 |
| % Sol. C: | 50 | 80 | 80 | 50 |

Under these conditions the pineal antigonadotropic peptide was eluted in a single 210 nm absorbance peak with a retention time of 36.8 min. By comparison, synthetic or natural pineal gland oxytocin was eluted in this chromatography with retention time of 34.3 min.

Determination of Primary Structure and Synthesis

Amino acids were quantitated by routine automated methods. A Beckman model 6300 autoanalyzer was utilized. Samples were hydrolyzed at 110° C. in 5.7N HCl for 24 h. The amino acids Cys and Met were determined by performic acid oxidation of the sample prior to hydrolysis with quantitation as cysteic acid and methionine sulfone. Amino guanidino propionic acid was incorporated as an internal standard. The major amino acids detected in hydroiysates of the residue obtained from the final HPLC step described above included: Thr, Phe, Pro, Tyr, Lys and Ser, ranked in order from the largest (Thr) to the smallest (Ser) amounts recovered (Benson, et al., In: Advances in Pineal Research, Vol. 4, Eds. R. J. Reiter & A. Lukaszyk, Libbey & Co. Ltd., pp. 99–111, 1990).

Primary sequence was determined on small quantities (<2 nM) of isolated peptide derived from the final HPLC purification step. Microsequence analysis was performed by automated methods well know to those skilled in the art. A pulsed liquid phase protein/peptide sequencer, Applied Biosystems model 477A was employed. The following primary sequence of the pineal antigonadotropin was revealed after twelve cycles:

NH₂-Ser-Phe-Pro-Thr-Thr-Lys-Thr-Tyr-Phe-Pro-COOH

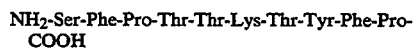

Single symbols: S F P T T K T Y F P

Peptide Synthesis

After its identification, the straight chain decapeptide of the present invention was readily synthesized by automated solid phase methods well known to those who are skilled in the art, which methods are set forth in the textbooks "Principles of Peptide Synthesis", Springer-Verlag, 1984; "Solid Phase Peptide Synthesis", J. M. Stewart and J. D. Young, Pierce Chemical Company, Rockford, Ill., 1984 (2nd ed.); G. Barany and R. B. Merrifield, "The Peptides", Ch 1 pp 1–285, Academic Press.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amid linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide.

Similarly, it is within the skill of the art to use the above-described automated solid phase peptide synthesis to synthesize a peptide having a sequences sufficiently homologous to the sequence: $NH_2$-Ser-Phe-Pro-Thr-Thr-Lys-Thr-Tyr-Phe-Pro-COOH, to yield a peptide having a correspondingly similar effectiveness to that of the peptide having the above-described seqence.

RECOMBINANT DNA TECHNOLOGY

Now that the peptide sequence $NH_2$-Ser-Phe-Pro-Thr-Thr-Lys-Thr-Tyr-Phe-Pro-COOH has been identified, it is within the skill of the art to identify and isolate the gene coding for that peptide, and prepare the peptide by means of recombinant DNA technology as an alternative to isolating it from the pineal gland or preparing it by means of automated solid phase peptide synthesis.

In order to prepare a peptide having the sequence $NH_2$-Ser-Phe-Pro-Thr-Thr-Lys-Thr-Tyr-Phe-Pro-COOH by means of recombinant DNA technology, the gene for the peptide must first be isolated from a cell's total DNA by screening a library of that cell's DNA. The DNA library is screened by use of a probe, a synthetic radiolabelled nucleic acid sequence which can be used to detect and isolate complementary base sequences by hybridization. Knowing the amino acid of the peptide, a probe for the gene can be designed based on the fact that each amino acid of the peptide is specified by a specific codon, or sequential grouping of three nucleotides. The possible nucleotides are adenine (A), guanine (G), cytosine (C), and thymine (T). The codons which are specific for each of the twenty amino acids found in proteins or peptides are listed below, together with the codons which signal termination of protein sythesis; although there is more than one codon for certain amino acids, no codon specifies more than one amino acid.

| AMINO ACID | CODONS |
|---|---|
| Alanine | GCA, GCC, GCG, GCU |
| Arginine | AGA, AGG, CGA, CGC, CGG, CGU |
| Asparagine | AAC, AAU |
| Aspartic Acid | GAC, GAU |
| Cysteine | UGC, UGU |
| Glutamic Acid | GAA, GAG |
| Glutamine | CAA, CAG |
| Glycine | GGA, GGC, GGG, GGU |
| Histidine | CAC, CAU |
| Isoleucine | AUA, AUC, AUU |
| Leucine | CUA, CUC, CUG, CUU, UUA, UUG |
| Lysine | AAA, AAG |
| Methionine | AUG |
| Phenylalanine | UUC, UUU |
| Proline | CCA, CCC, CCG, CCU |
| Serine | UCA, UCC, UCG, UCU, AGC, AGU |
| Threonine | ACA, ACC, ACG, ACU |
| Tryptophan | UGG |
| Tyrosine | UAC, UAU |
| Valine | GUA, GUC, GUG, GUU |
| Termination Codons: | UAA, UAG, UGA |

Because some amino acids have several possible codons and it is not initially known which of the possible codons will actually code for an amino acid, a set of probes can be designed that covers all possible codons for each amino acid comprising the peptide; such a set of probes is known as a "fully degenerate" set of probes.

A library to be screened can be a genomic library (gDNA), which contains a set of all the DNA sequences found in an organism's cells, or a complementary DNA (cDNA) library, which is much smaller and less complex than a gDNA library, as is used frequently when the tissue source for a given gene is known. Because the peptide was isolated from the pineal gland, the tissue source is known, and therefore it would be much more efficient to screen the cDNA library for the pineal gland rather than screening the genomic library.

When the gene for the peptide is identified and isolated from the cDNA library, it is cloned by inserting or splicing it into a plasmid or vector. The recombinant plasmid or vector with the inserted gene—the cloned gene—is then introduced, or "transfected", into a host cell. The host cell at that point is "transformed" or "transvected". The vector or plasmid is the carrier which brings the DNA or gene of interest into the host cell, and allows the DNA to grow and replicate as the host cell grows and replicates, eventually causing the host cell to express or produce the peptide.

Peptide effectiveness, whether isolated from the pineal gland or produced by means of automated solid phase peptide synthesis or recombinant DNA technology, can be evaluated by means of the in vivo and in vitro procedures described as follows.

ASSAY PROCEDURES

In Vivo

The neurotropic pineal antigonadotropin of the present invention was assayed in vivo, as is described below. Natural and synthetic analogs were injected into male and female rats and mice in graded doses. Antigonadotropic effects were assessed after a period of chronic daily subcutaneous injection in a variety of solvents/carriers, e.g. physiological saline or corn oil. After a period of two to four weeks the antigonadotropic effect was manifested as reductions of pituitary and blood levels of gonadotropins and prolactin, coupled with significant reductions in pituitary, gonadal and accessory reproductive organ weights, i.e. weights of the testes, prostate gland and seminal vesicles in males and ovaries and uterus in females. Additionally, blood levels of the gonadal steroids (testosterone in males and estrogens in females) were reduced.

In male mice such changes in reproductive hormones and organ weights are generally associated with significant increases in anterior pituitary contents of dopamine (Benson, B. and I. Ebels, In: *The Pineal Gland*, Vol. II, Ed. by R. J. Reiter, CRC Press Inc., Boca Raton, pp. 165–187, 1981; Benson, B. et al., In: *Role of Peptides and Proteins in Reproduction*, Ed. by S. M. McCann and D. S. Dhindsa, Elsevier Sci. Pub. Co., Inc., pp. 111–130, 1983).

Acute effects of subcutaneous injections of the pineal antigonadotropin (PAG) were also readily demonstrated. Provided in the table below is an example in which a single injection of 25 nanograms in mice produced a significant increase in anterior pituitary dopamine content:

Effects on Pituitary Dopamine Content

| Treatment | Postinjection Time (min) | | |
|---|---|---|---|
| | 0' | 15' | 30' |
| Saline | 0.545 ± 0.039 | 0.551 ± 0.043 | 0.552 ± 0.049 |
| PAG | 0.539 ± 0.046 | *0.795 ± 0.064 | *1.801 ± 0.126 |

Values are nanograms per mg of pituitary.
PAG = pineal antigonadtropin.
* = $p < 0.05$ vs. control;
** = $p < 0.01$ Intravenous or intracerebroventricular injections of the natural or synthetic pineal antigonadotropin readily produced demonstrable inhibitory effects on pituitary secretion of LH and PRL. Intracerebroventricular infusions inhibited release of pituitary LH, reducing both the amplitude and frequency of pulsatile LH release into the blood.

For intravenous peptide injections anesthetized rats were fitted surgically with indwelling intra-arterial cannulae 24 hours before the tests. The next day samples of arterial blood were withdrawn from the unanesthetized rats immediately before and after the injection of graded doses of the pineal antigonadotropin. Prolactin and LH were measured in the blood samples by standard double antibody radioimmunoassay with kits provided by the National Hormone and Pituitary Program. The acute effects of 5.0 micrograms of the antigonadotropin are illustrated in the table below:

Effects on serum LH (ng/ml)

| Treatment | Postiniection Time (min) | | | | |
|---|---|---|---|---|---|
| | 0' | 15' | 30' | 45' | 60' |
| Saline | 0.26 | 0.25 | 0.28 | 0.25 | 0.23 |
| PAG (1) | 0.25 | 0.21 | 0.15 | 0.10 | 0.14 |
| PAG (2) | 0.26 | 0.20 | 0.15 | 0.12 | 0.11 |

Effects on Serum PRL (% of Initial Control Value)

| Treatment | Postinjection Time (min) | | | | |
|---|---|---|---|---|---|
| | 0' | 15' | 30' | 45' | 60' |
| PAG (1) | 100 ± 11 | 55 ± 6 | 38 ± 6 | 31 ± 4 | 22 ± 5 |
| PAG (2) | 100 ± 8 | 44 ± 6 | 30 ± 3 | 25 ± 3 | 32 ± 6 |

PAG (1) = natural peptide; PAG (2) = synthetic peptide;

Values for LH are expressed as the National Institutes of Health reference standard LH-RP-2. Means±S.E.M. are indicated (n=5)

In Vitro

The pineal antigonadotropic decapeptide stimulates the release of dopamine from the rat hypothalamus in vitro. Rat hypothalamic median eminence strips were rapidly dissected and placed in culture plates containing 100 μl of a Kreb's solution saturated with $O_2$ in accord with the procedure described in Racke, K. and E. Muscholl, J. of Neurochemistry 46:745, 1986. The median eminence strips were maintained at 37° C. under 95% $O_2/5\%CO_2$ in a Dubnoff shaking incubator. The media were replaced after a ten minute pre-incubation period. 50 μl samples were taken at 30, 60 and 90 min of incubation for catecholamine determination, with replacement of the removed media. 20 μl of 0.1M perchloric acid were added to each sample before storage at −20°. Media contents of dopamine, norepinephrine and various indoleamine and catecholamine metabolites were determined by HPLC coupled with electrochemical detection in accord with the procedure described in Gregory, V. M., B. Larsen and B. Benson, J. of Chromatography 345:140–144, 1985. As shown in the following table the addition of the synthetic decapeptide effectively stimulates the release of dopamine into the incubation medium:

| Treatment | Incubation Time (min) | | |
|---|---|---|---|
| | 30' | 60' | 90' |
| Control | 15.8 ± 1.7 | 42.9 ± 3.6 | 75.5 ± 9.2 |
| PAG ($10^{-7}$ M) | 27.2 ± 2.1 | 61.5 ± 5.3 | 109.3 ± 10.8 |
| PAG ($10^{-5}$ M) | 35.2 ± 7.6 | 100.2 ± 13 | 182.9 ± 13.7 |

Means ± S.E. are shown for five samples.
*Values represent accumulative pg/μl.

UTILITIES

The natural and synthetic compounds of this invention produce antigonadotropic effects mediated by increased release of the catecholaminergic hypothalamic neurotransmitter dopamine. A number of uses are therefore embodied in and flow therefrom. These relate to the fields of reproductive endocrinology, gynecology, oncology, contraception, animal husbandry, veterinary science, neurology, and internal medicine.

Use as an Antigonadotropic Agent in Humans

The decapeptides of this invention, or appropriate nontoxic salts or effective synthetic analogs thereof, can be administered to female humans for treatment of precocious puberty; contraception; ovulation prevention or delay; synchronization of ovulation; treatment of ovarian and mammary cystic disease; treatment of premenstrual syndrome; the regulation of elevated gonadotropins during menopause; treatment of gonadotropin-, prolactin- and/or steroid-dependent breast tumors; treatment of endometriosis; uterine leiomyoma; uterine carcinoma; hyperprolactinemia associated dysmenorrhea or amenorrhea; pituitary lactotroph microadenoma; and during early first trimester as an abortifacient.

In male humans the decapeptides can be used as therapy for benign prostatic hypertrophy; treatment of prostatic carcinoma; contraception; therapy for diseases which result from excessive gonadal hormone production, e.g. precocious puberty; and hyperprolactinemia associated gynecomastia and impotency.

Use as an Antigonadotropic Agent in Animals

The decapeptide of the present invention has a number of uses in animals, for example, use for ovulation prevention or delay; pregnancy termination in domestic animals or pets; heat or estrus suppression; induction of luteolysis; functional castration in male food producing animals; treatment of endometriosis; and suppression of proestrous bloody discharge in dogs. The decapeptide can also be used as a drug in common laboratory rodents, rabbits, guinea pigs, dogs, cats, pigs, primates and large farm animals in experiments where reduced gonadotropins and prolactin are experimentally desirable.

Use as a Dopamine Releasing Agent

The decapeptide of this invention can be used as a neurotropic therapeutical agent in the treatment of Parkinson's or Alzheimer diseases in humans in which catecholamine release is deficient.

Other uses in humans include treatment of sleep-wake disorders; treatment of affective and psychotic disorders associated with catecholamine deficiency; and as a therapeutical agent in the treatment of schizophrenia.

Use as an Antihypertensive Agent

The decapeptide of this invention can be used as an antihypertensive agent since it lowers blood pressure. It can be used to reduce renal glomerular filtration rate and to control sodium excretion through intra- or extra-renal regulators, e.g. adrenal release of aldosterone or pituitary release of antidiuretic hormone.

METHODS OF USE

In the practice of methods to use the compounds of the present invention, an effective amount of the peptide, synthetic analogue, pharmaceutically acceptable nontoxic salt thereof, or pharmaceutical composition containing same is administered to the subject in need of, or desiring, such treatment. These compounds or compositions may be administered by any of a variety of routes depending upon the specific end use, including orally, intravenously, parenterally (including subcutaneous, intramuscular and intravenous administration), transdermally, nasally, or by suppository.

The most suitable route in any given case will depend upon the use, particular active ingredient, the subject involved, and the judgment of the medical practitioner. The compound or composition may also be administered by means of controlled-release, depot implant or injectable formulations as described more fully here below.

In general for the uses herein above described, it is expected that the active ingredient will be administered in amounts between about 0.001 and 5 mg/kg body weight. Preferably, for human therapy, it is expected that the active ingredient will be administered in the range of from about 0.01 to about 1 mg/kg/day. This administration may be accomplished by a single administration, by distribution over several applications or by slow release in order to achieve the most effective results.

The exact dose and regimen for administration of these compounds and compositions will necessarily be dependent upon the needs of the individual subject being treated, the type of treatment, the degree of affliction or need and, of course, the judgment of the medical practitioner. In general, parental administration requires lower dosage than other methods of administration which are more dependent upon absorption.

PHARMACEUTICAL COMPOSITIONS

A further aspect of the present invention relates to pharmaceutical compositions containing as active ingredients a compound of the present invention which compositions comprise such compound in admixture with a pharmaceutically acceptable, nontoxic carrier. As mentioned above, such compositions may be prepared for use for parental (subcutaneous, intramuscular and intravenous) administration, particularly in the form of liquid solutions or suspensions, for suppositories, for oral administration particularly in the form of tablets or capsules, or intranasally particularly in the form of powders, nasal drops or aerosols.

Further details of the preparation of pharmaceutical compositions and formulations, preparation of pharmaceutically acceptable nontoxic salts, and the synthesis of peptides and peptide analogues can be found in U.S. Pat. No. 4,801,577, issued Jan. 31, 1989 to Nestor, Jr., et al., which is hereby incorporated by reference herein. It is expected that the compounds of the present invention can be formulated into pharmaceutical compositions, synthesized, and converted into salts in a manner similar to the peptides disclosed in the patent to Nestor, Jr., et al.

Although the invention has been described with regard to its preferred embodiments, it should be understood that changes and modifications as would be obvious to one having the ordinary skill in this art without departing from the scope of the invention which is set forth in the claims which are appended hereto.

---

I claim:

1. A peptide having the sequence NH₂-Ser-Phe-Pro-Thr-Thr-Lys-Thr-Tyr-Phe-Pro-COOH, or a pharmaceutically acceptable nontoxic salt thereof.

2. A pharmaceutical composition for regulating the release of dopamine and for regulating the release of gonadotropins and prolactin, comprising as an active ingredient an effective amount of a peptide having the sequence NH₂-Ser-Phe-Pro-Thr-Thr-Lys-Thr-Tyr-Phe-Pro-COOH, or a pharmaceutically acceptable nontoxic salt thereof, in association with a major amount of a nontoxic diluent.

3. The composition of claim 2, wherein said composition is in the form of a pill, tablet, capsule, liquid, or sustained release tablet for oral administration.

4. The composition of claim 2, wherein said composition is in the form of a liquid capable of being administered intravenously, subcutaneously, parenterally, or intraperitoneally.

5. The composition of claim 2, wherein said composition is in the form of an injectable suspension comprising said peptide and a bioerodible, biocompatible polymer matrix capable of effecting sustained release of said decapeptide.

6. The composition of claim 2, wherein said composition is in the form of a peptide/bioerodible, biocompatible implant.

7. The composition of claim 2, wherein said composition is a transdermal patch or transmucosal patch.

8. A method for regulating the secretion of gonadotropins and prolactin in mice and rats, the method comprising administering an effective amount of a peptide having the sequence NH₂-Ser-Phe-Pro-Thr-Thr-Lys-Thr-Tyr-Phe-Pro-COOH, or a pharmaceutically acceptable nontoxic salt thereof.

9. The method of claim 6 wherein the effective amount is in the range of about 0.001 to 5 mg/kg body weight.

10. The method of claim 9 wherein the effective amount is in the range of about 0.01 to 1 mg/kg body weight.

* * * * *